United States Patent
Aoki

(10) Patent No.: US 10,004,920 B2
(45) Date of Patent: Jun. 26, 2018

(54) PARTICLE BEAM ROTATIONAL IRRADIATION APPARATUS AND PARTICLE BEAM THERAPY SYSTEM

(71) Applicant: Ryusuke Aoki, Tokyo (JP)

(72) Inventor: Ryusuke Aoki, Tokyo (JP)

(73) Assignee: MITSUBISHI ELECTRIC CORPORATION, Chiyoda-Ku, Tokyo (JP)

(*) Notice: Subject to any disclaimer, the term of this patent is extended or adjusted under 35 U.S.C. 154(b) by 287 days.

(21) Appl. No.: 14/647,177

(22) PCT Filed: Feb. 7, 2013

(86) PCT No.: PCT/JP2013/052810
§ 371 (c)(1),
(2) Date: May 26, 2015

(87) PCT Pub. No.: WO2014/122745
PCT Pub. Date: Aug. 14, 2014

(65) Prior Publication Data
US 2015/0297918 A1    Oct. 22, 2015

(51) Int. Cl.
*A61N 5/10*    (2006.01)

(52) U.S. Cl.
CPC .... *A61N 5/1081* (2013.01); *A61N 2005/1087* (2013.01)

(58) Field of Classification Search
CPC .......................................... A61N 5/10–5/1084
See application file for complete search history.

(56) References Cited

U.S. PATENT DOCUMENTS

| | | |
|---|---|---|
| 2004/0061077 A1 | 4/2004 | Muramatsu et al. |
| 2004/0061078 A1 | 4/2004 | Muramatsu et al. |
| 2004/0111134 A1 | 6/2004 | Muramatsu et al. |

FOREIGN PATENT DOCUMENTS

| | | |
|---|---|---|
| EP | 1 402 923 A1 | 3/2004 |
| JP | 2000-140134 A | 5/2000 |
| JP | 2001-259058 A | 9/2001 |
| JP | 2001-321453 A | 11/2001 |
| JP | 2009-148325 A | 7/2009 |

(Continued)

OTHER PUBLICATIONS

International Search Report (PCT/ISA/210) dated Mar. 5, 2013, by the Japanese Patent Office as the International Searching Authority for International Application No. PCT/JP2013/052810.

(Continued)

*Primary Examiner* — Thaddeus Cox
(74) *Attorney, Agent, or Firm* — Buchanan Ingersoll & Rooney PC

(57) ABSTRACT

A particle beam rotational irradiation apparatus includes: a frame that supports an irradiation nozzle and rotates; an irradiation-nozzle support member that is provided on an inner-circumference side of the frame and supports the irradiation nozzle; a movable floor that has a roller movable in a circumferential direction centering on a rotation axis of the frame; and a movable-floor rail that is provided in the circumferential direction on the inner-circumference side of the frame and supports the roller; wherein the irradiation-nozzle support member and the movable floor have respective coupling portions that are attachable/detachable to/from each other in the circumferential direction centering on the rotation axis of the frame.

17 Claims, 4 Drawing Sheets

(56) References Cited

FOREIGN PATENT DOCUMENTS

JP    2010-75512 A    4/2010
JP    2011-156263 A   8/2011

OTHER PUBLICATIONS

First Office Action dated Dec. 20, 2016, by the Chinese Patent Office in corresponding Chinese Patent Application No. 201380072215.8, and an English Translation of the Office Action. (12 pages).
Extended European Search Report dated Sep. 22, 2016, issued by the European Patent Office in corresponding European Application No. 13874638.3. (7 pages).
Office Action (English translation of Examination Report) dated Oct. 12, 2015, by the Taiwanese Patent Office in corresponding Taiwanese Patent Application No. 102117173. (11 pages).
Second Office Action dated May 26, 2017 in corresponding Chinese Patent Application No. 201380072215.8, and an English translation thereof (11 pages).

PRIOR ART

PARTICLE BEAM ROTATIONAL IRRADIATION APPARATUS AND PARTICLE BEAM THERAPY SYSTEM

TECHNICAL FIELD

The present invention relates to a particle beam therapy system used for cancer therapy and the like, and in particular, to a particle beam rotational irradiation apparatus that can radiate in a rotatable manner around a patient.

BACKGROUND ART

In recent years, among radiation therapy systems for the purpose of cancer therapy, there have been advanced development and/or construction of a cancer therapy system that utilizes a particle beam of proton, heavy ion, etc. (called, in particular, as a particle beam therapy system) As is well known, according to a particle beam therapy utilizing the particle beam, a cancer diseased site can be irradiated in a concentrated manner as compared to the conventional radiation therapy utilizing an X-ray, a γ-ray, etc. and thus it is possible to perform the therapy without affecting normal cells.

Charged particles formed into a beam (referred to also as a charged particle beam or the particle beam) that is obtained by circularly accelerating the charged particles by an accelerator (circular accelerator) such as a synchrotron, etc. and taking out the charged particles (mostly, protons or carbon ions) accelerated up to a high energy from the circular trajectory thereof, are transported using a beam transport system so as to be applied to a physical experiment in which an intended object is irradiated therewith or a particle beam therapy such as a cancer therapy, etc. In the cancer therapy by the accelerated charged particles, that is, in the particle beam therapy, in order to keep vital organs away or to prevent normal tissues from being damaged at the time of the therapy, changing a direction of the irradiation is generally performed. In order to irradiate the patient from an arbitrary direction, a particle beam rotational irradiation apparatus is provided in many cases. The particle beam rotational irradiation apparatus (called also as a rotational irradiation apparatus, when appropriate) is provided with an irradiation nozzle that is mounted on a rotary gantry and radiates the particle beam. The rotary gantry is configured to rotate the irradiation nozzle that radiates the particle beam so that the irradiation nozzle can radiate the charged particle beam to the patient from an arbitrary rotation angle.

In the case where the irradiation nozzle is rotated so that it can radiate from an arbitrary angle to the patient, a treatment table on which the patient is secured is required to be fixed whereas the irradiation nozzle is rotating, so that the treatment table results in a configuration that protrudes from the side of a stationary portion provided in the building side. Thus, although an access floor is provided for allowing a doctor, a radiological technologist or the like who performs the therapy to always approach the patient so as to perform works, the access floor is required to always keep a function as a floor, regardless of the rotation angle of the rotary gantry.

Although the access floor is required as described above, because the access floor interferes with a passing area of the irradiation nozzle mounted on the rotary gantry, such an interfering area between the irradiation nozzle and the access floor has to be evacuated off during passing of the irradiation nozzle. Thus, it is necessary to provide an access floor that can be retracted only when the irradiation nozzle is going to pass through the access floor (hereinafter, referred to as a movable floor) and an access floor that is fixed.

For example, in Patent Document 1, there is described a particle beam rotational irradiation apparatus provided with an openable floor. FIG. 7 is a diagram showing the conventional-type particle beam rotational irradiation apparatus. The particle beam rotational irradiation apparatus placed in a building 106 includes a frame 101, a rotary ring 102, a rotation driving device 103, a gantry roller 104, a braking device 105, a beam transport instrument 107, an irradiation nozzle 108, a treatment table 109, a movable floor 110 and an access floor 115. The frame 101, the rotary ring 102, the rotation driving device 103 and the gantry roller 104 are coupled together, so that the frame 101 rotates as the rotation driving device 103 rotates. When the irradiation nozzle 108 becomes close, by its rotation, to the movable floor 110, divided movable floors that form the movable floor 110 are going to be retracted one by one in the direction of the rotation axis. With the progress of rotation of the irradiation nozzle 108, the movable floor 110 is retracted in the direction of the rotation axis.

Meanwhile, in Patent Document 2, there is described, as another type of particle beam rotational irradiation apparatus, a particle beam rotational irradiation apparatus of a so-called corkscrew type. In this corkscrew-typo particle beam rotational irradiation apparatus, charged particle beam is guided in such a manner that the charged particle beam is once deflected using two bending magnets so that its beam transport line becomes perpendicular to the rotation axis of the rotary gantry, and is thereafter deflected again using two bending magnets so that the charged particle beam becomes directed to an isocenter (intersection point between the gantry rotation axis and the beam axis, that is a reference of irradiation target) within a plane perpendicular to the central axis of the gantry. Such a beam transport line allows the rotary gantry to be shorter in its length with respect to the direction of the rotation axis. Note that the bending magnet is usually a two-pole electromagnet that has two poles.

CITATION LIST

Patent Document

Patent Document 1: Japanese Patent Application Laid-open No. 2001-259058 (FIG. 1, FIG. 3)

Patent Document 2: Japanese Patent Application Laid-open No. 2000-140134 (FIG. 1, FIG. 2)

SUMMARY OF THE INVENTION

Problems to be Solved by the Invention

Using FIG. 8, differences between the conventional-type rotational irradiation apparatus 70 as in Patent Document 1 and the corkscrew-type rotational irradiation apparatus 80 as in Patent Document 2 will be described. The conventional rotational irradiation apparatus 70 is provided with the beam transport instrument 107 having three bending magnets 71a, 71b, 71c. The corkscrew-type rotational irradiation apparatus 80 is provided with a beam transport instrument (beam transport line) having four bending magnets 71a, 71b, 71c, 71d. In FIG. 8, indicated at numerals 72, 73 and 74 are a gantry rotation axis, a gantry outer frame and an isocenter, respectively. A major difference between these rotational irradiation apparatuses 70, 80 resides in their widths in the direction of the gantry rotation axis 72, such that the width L2 in the direction of the rotation axis of the corkscrew-type rotational irradiation apparatus 80 is largely narrower than the width L1 in the direction of the rotation axis of the conventional rotational irradiation apparatus 70. The corkscrew-type rotational irradiation apparatus 80 is compact in comparison to the conventional-type rotational irradiation apparatus 70. Thus, employing the corkscrew-type rotational irradiation apparatus 80 makes it possible to reduce the facility area of the particle beam therapy system as a whole, and is thus very useful in terms of cost and processes therefor.

Although the corkscrew-type particle beam rotational irradiation apparatus as in Patent Document 2 is made smaller in the direction of the rotation axis of the rotary gantry, the shape of its irradiation nozzle and the space for the treatment table do not differ from those of the conventional-type particle beam rotational irradiation apparatus, so that there is no difference in space for the access floor placed around the treatment table. Accordingly, when the movable floor in Patent Document 1 is to be placed in the corkscrew-type particle beam rotational irradiation apparatus in Patent Document 2, no retraction space is provided for the movable floor. Thus, in the corkscrew-type particle beam rotational irradiation apparatus, it is unable to employ the technique of the movable floor in Patent Document 1.

This invention is purported to provide a particle beam rotational irradiation apparatus that is provided with, even if it is a corkscrew-type particle beam rotational irradiation apparatus, a movable floor that is retractable at the time of movement of the irradiation nozzle.

Means for Solving the Problems

A particle beam rotational irradiation apparatus according to the invention is characterized by comprising: an irradiation nozzle that radiates a charged particle beam to an irradiation target; a frame that supports the irradiation nozzle and rotates centering on an isocenter that is an irradiation reference for the charged particle beam; an irradiation-nozzle support member that is provided on an inner-circumference side of the frame and supports the irradiation nozzle; a movable floor that has a roller movable in a circumferential direction centering on a rotation axis of the frame; and a movable-floor rail that is provided in the circumferential direction on the inner-circumference side of the frame, and supports the roller; wherein the irradiation-nozzle support member and the movable floor have their respective coupling portions that are attachable/detachable to/from each other in the circumferential direction centering on the rotation axis of the frame.

Effect of the Invention

In accordance with the particle beam rotational irradiation apparatus according to the invention, when the irradiation nozzle comes close to the movable floor, the movable floor and the irradiation nozzle are unified together through the irradiation-nozzle support member, so that the movable floor moves together with the irradiation nozzle in the circumferential direction. Thus, even if it is of a corkscrew type, the movable floor that is retractable at the time of movement of the irradiation nozzle can be placed in the frame.

MODES FOR CARRYING OUT THE INVENTION

Embodiment 1

Figure 1:
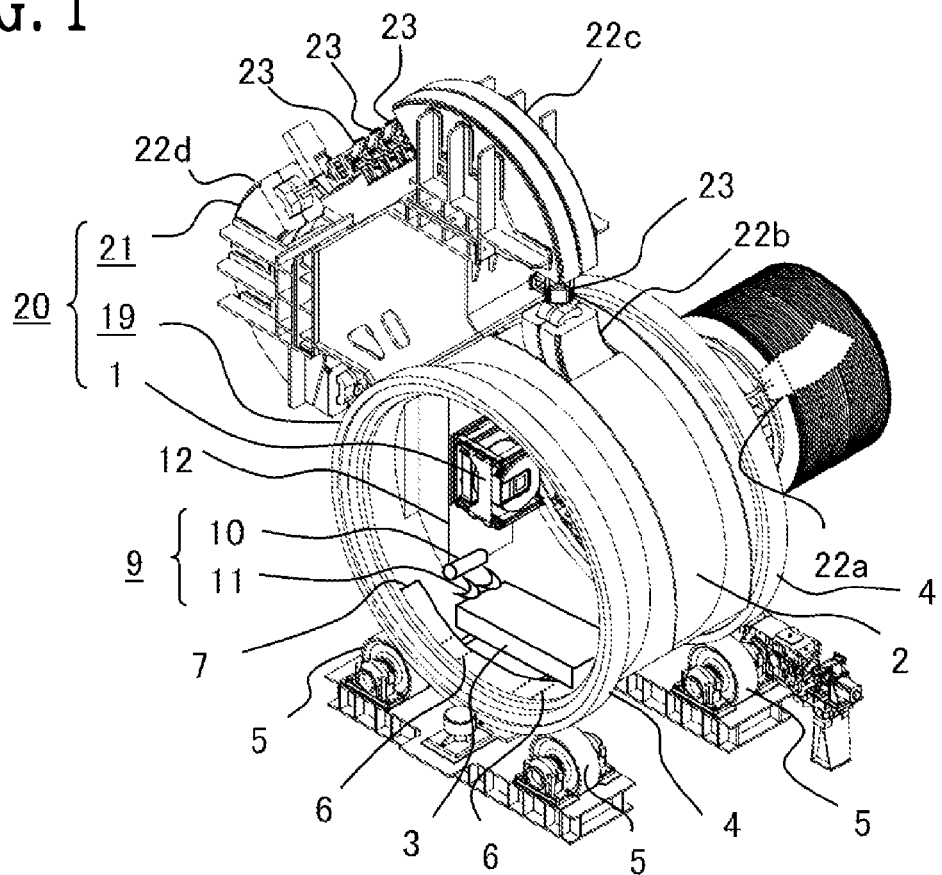
FIG. 1 is a diagram showing a particle beam rotational irradiation apparatus according to Embodiment 1 of the invention.
Figure 2:
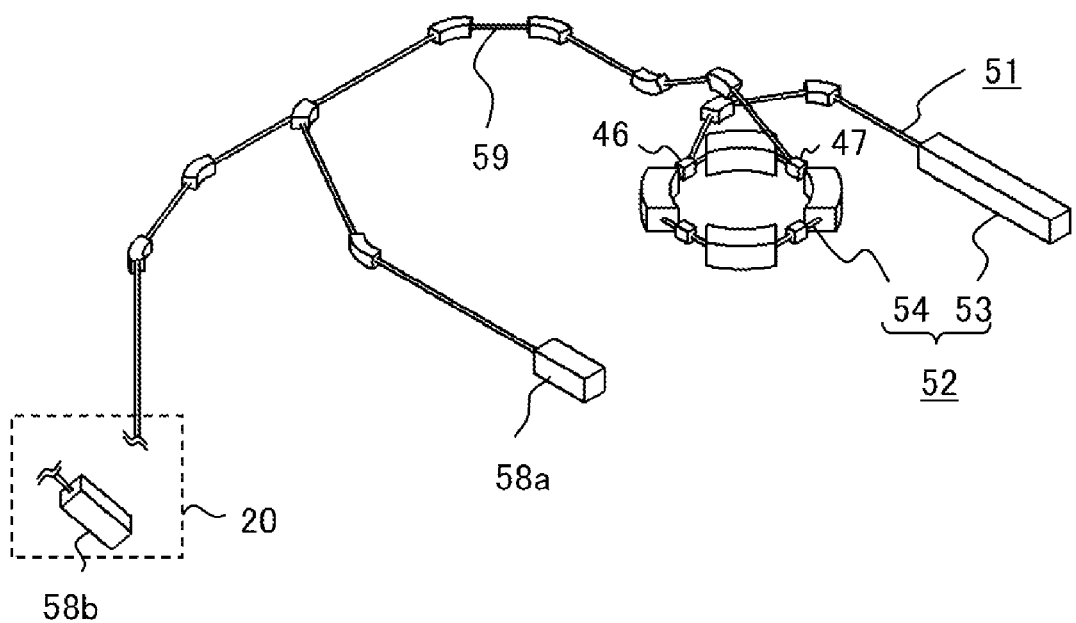
FIG. 2 is a schematic configuration diagram of a particle beam therapy system according to Embodiment 1 of the invention.
Figure 3:
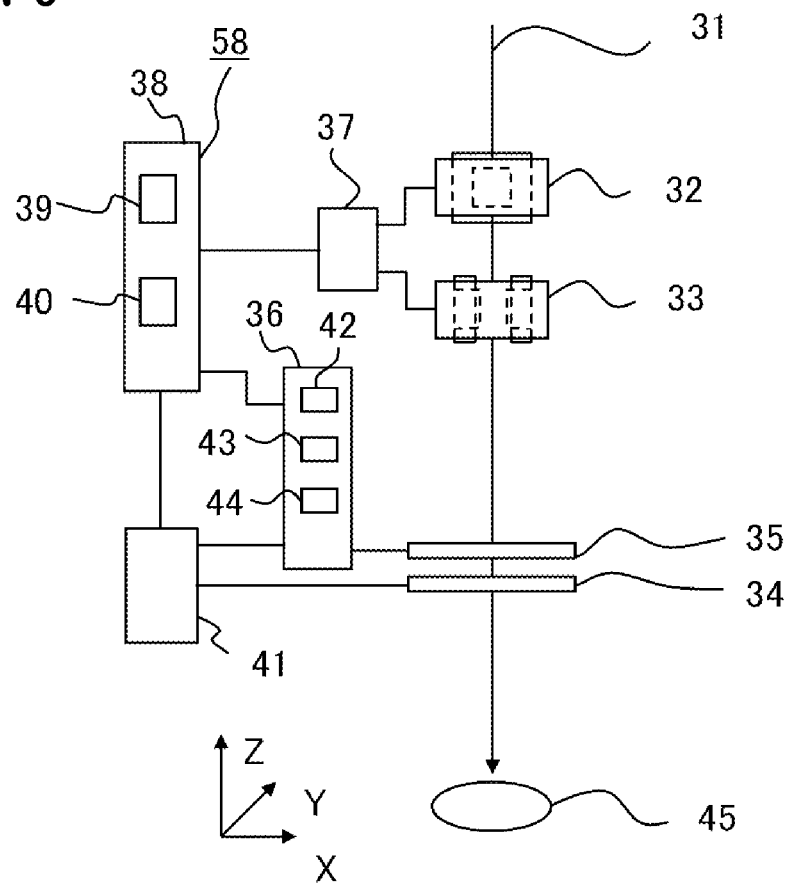
FIG. 3 is a diagram showing a configuration of a particle beam irradiation apparatus in FIG. 2.
Figure 4:
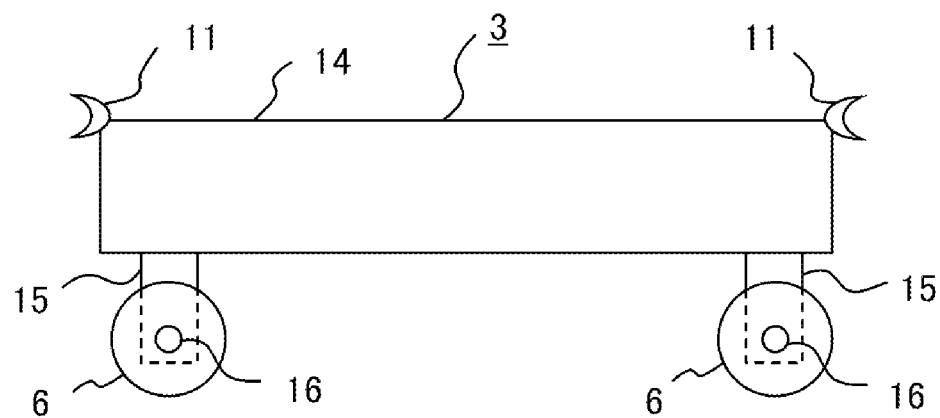
FIG. 4 is a side view showing a movable floor according to Embodiment 1 of the invention.
Figure 5:
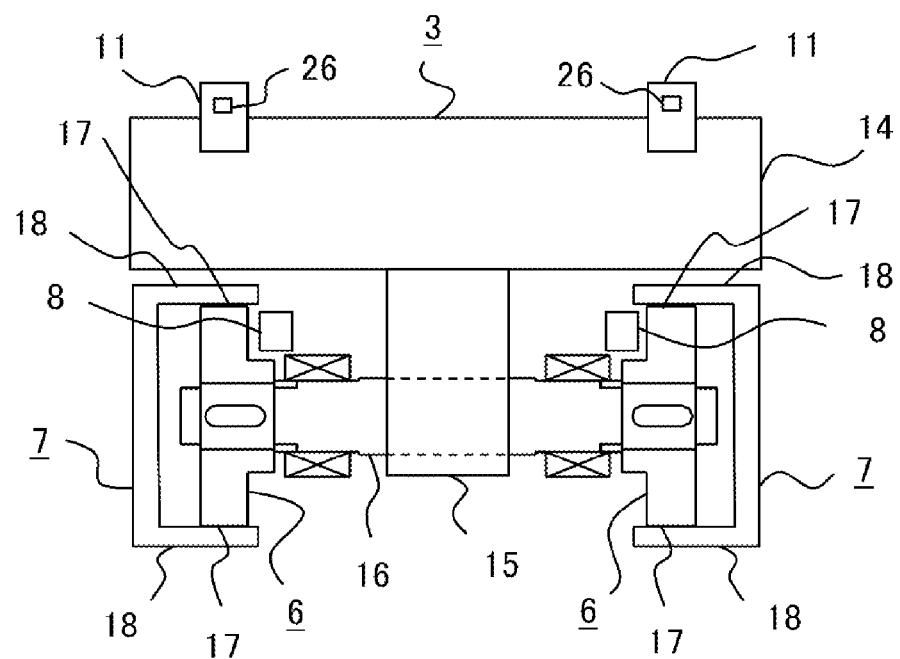
FIG. 5 is a diagram showing the movable floor and a movable-floor rail according to Embodiment 1 of the invention.
Figure 6:
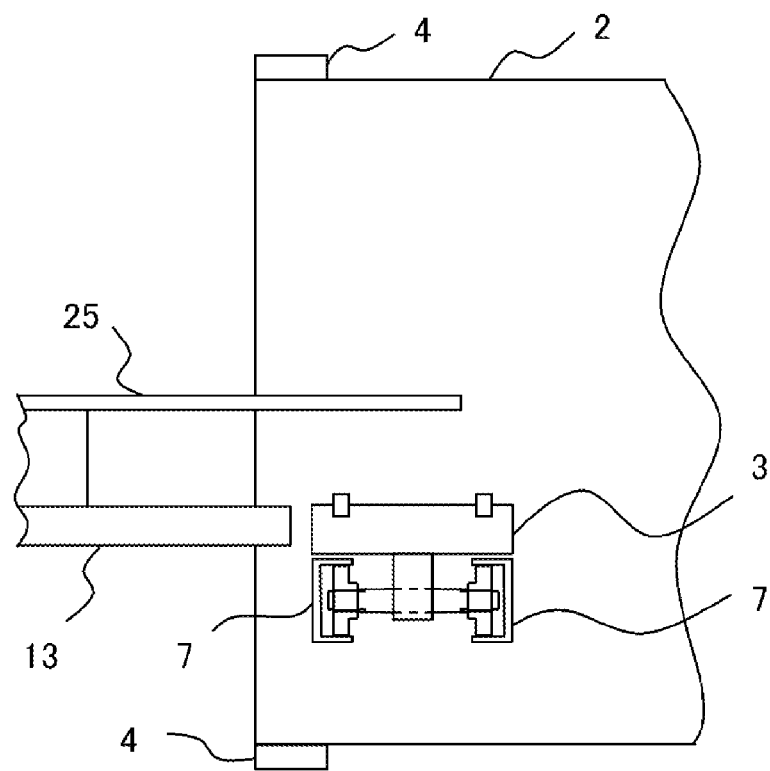
FIG. 6 is a diagram showing a non-interfering position of the movable floor according to Embodiment 1 of the invention.
Figure 7:
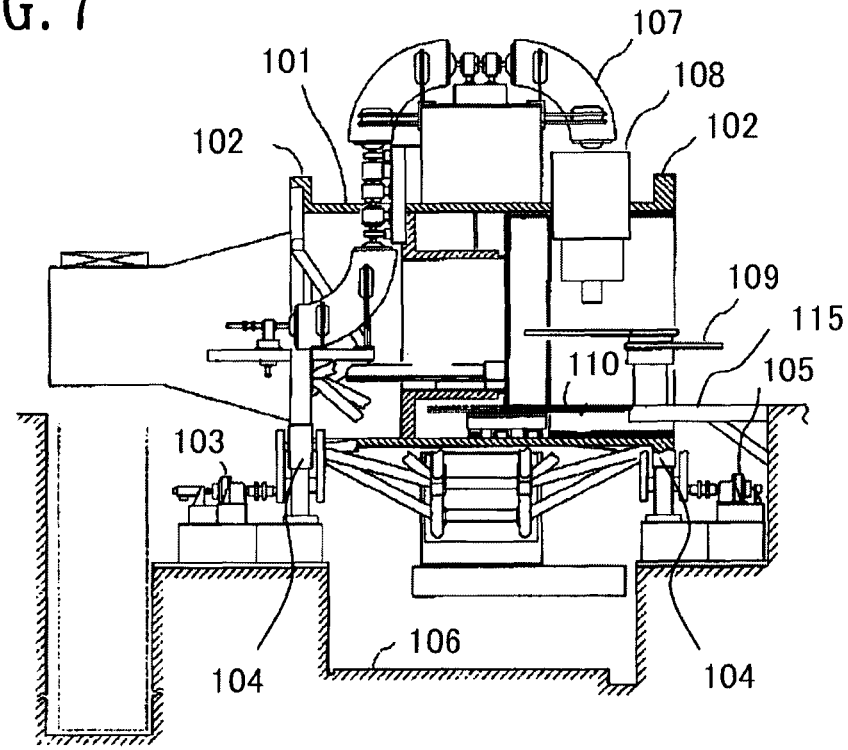
FIG. 7 is a diagram showing a conventional-type particle beam rotational irradiation apparatus.

FIG. 1 is a diagram showing a particle beam rotational irradiation apparatus according to Embodiment 1 of the invention. FIG. 2 is a schematic configuration diagram of a particle beam therapy system according to Embodiment 1 of the invention, and FIG. 3 is a diagram showing a configuration of a particle beam irradiation apparatus in FIG. 2. FIG. 4 is a side view showing a movable floor according to Embodiment 1 of the invention, and FIG. 5 is a diagram showing the movable floor and a movable-floor rail according to Embodiment 1 of the invention. FIG. 6 is a diagram showing a non-interfering position of the movable floor according to Embodiment 1 of the invention. The particle beam rotational irradiation apparatus 20 includes an irradiation nozzle 1 that radiates a charged particle beam 31 to a patient 45, a beam transport portion 21 that transports the charged particle beam 31, and a rotary gantry 19 that supports the irradiation nozzle 1 and the beam transport portion 21 and rotates. The rotary gantry 19 includes a gantry frame 2, a movable floor 3, a bearing ring 4, a bearing roller 5, a movable-floor rail 7 and an irradiation-nozzle support member 12. The gantry frame 2 is a structure that supports the irradiation nozzle 1 and the beam transport portion 21. The beam transport portion 21 has four bending magnets 22a, 22b, 22c, 22d, for example, and a plurality of four-pole electromagnets 23. Note that in FIG. 1, the bending magnet 22a, although not visible from the outside, is shown in white outlined by a broken line. The irradiation nozzle 1 is a configuration device of a particle beam irradiation apparatus 58 that is mounted on the rotary gantry 19, and corresponds to a portion of the apparatus other than, for example, an irradiation control computer 39 to be described later.

Figure 8:
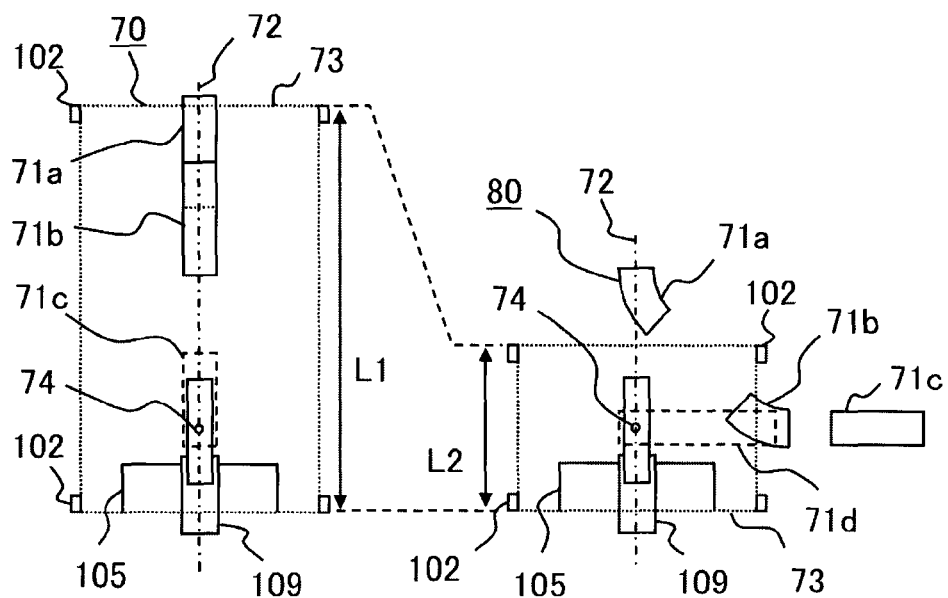
FIG. 8 is a diagram for comparing between a conventional-type rotational irradiation apparatus and a corkscrew-type rotational irradiation apparatus.

The beam transport portion 21 has the plurality of bending magnets 22a, 22b, 22c, 22d at the positions deviated from a plane including the rotation axis of the rotary gantry 19 and the irradiation axis of the irradiation nozzle 1. This arrangement of the bending magnets 22a, 22b, 22c, 22d is similar to that in the rotational irradiation apparatus 80 in FIG. 8. The plane including the rotation axis of the rotary gantry 19 and the irradiation axis of the irradiation nozzle 1 includes the gantry rotation axis 72 and the isocenter 74 in FIG. 8, and is a plane perpendicular to the paper plane of FIG. 8 (will be called as a beam transport plane). If the bending magnets 71a, 71b, 71c, 71d in FIG. 8 are instead read as the bending magnets 22a, 22b, 22c, 22d, beam paths of the charged particle beam at all of the bending magnets 22a, 22b, 22c, 22d are deviated from the beam transport plane, and thus all of the bending magnets 22a, 22b, 22c, 22d are arranged so that their beam paths are deviated from the beam transport plane. The beam path of the bending magnet 22a is bent so as to be deviated from the beam transport plane. Accordingly, the beam transport portion 21 has the plurality of bending magnets 22a, 22b, 22c, 22d that are arranged so that a beam path of the charged particle beam is once deviated from the beam transport plane that includes the rotation axis of the rotary gantry 19 and the irradiation axis of the irradiation nozzle 1 and then returns to the beam transport plane again.

The irradiation-nozzle support member 12 and the movable floor 3 have coupling portions 9 for their mutual coupling. On the irradiation-nozzle support member 12, there is provided a first engaging portion 10 that constitutes the coupling portion 9 to be coupled to the movable floor 3, and on the movable floor 3, there is provided a second engaging portion 11 that constitutes the coupling portion 9 to be coupled to the irradiation-nozzle support member 12. For allowing the coupling even if the movable floor 3 comes close from either direction of the clockwise direction or the counter-clockwise direction, the irradiation-nozzle support member 12 has the first engaging portion 10 at each of its both end portions. As shown in FIG. 4, for allowing the coupling even if the irradiation nozzle 1 comes close from either direction of the clockwise direction or the counter-clockwise direction, the movable floor 3 has the second engaging portion 11 at each of its both end portions.

As shown in FIG. 4 and FIG. 5, the movable floor 3 includes a movable floor plate 14, movable-floor rollers 6, shafts of the movable-floor rollers 16, shaft support portions 15 for supporting the shafts 16, brakes 8 for stopping rotation of the movable-floor rollers 6, and the aforementioned first engaging portions 11 as the coupling portions 9. The movable floor 3 is placed so that it moves in a circumferential direction centering on the rotation axis of the rotary gantry 19. Specifically, the shafts 16 of the movable-floor rollers 6 are placed in parallel with the rotation axis of the rotary gantry 19 so that the movable-floor rollers 6 of the movable floor 3 are turnable in the circumferential direction of the rotary gantry 19. On the gantry frame 2, in order for the movable floor 3 to be retracted in the circumferential direction of the rotary gantry 19 when the irradiation nozzle 1 moves in the circumferential direction of the rotary gantry 19, there is the movable-floor rail 7 serving as a guide for the movable-floor rollers 6.

As shown in FIG. 5, in order for the movable floor 3 not to derail from the gantry frame 2 when the movable floor 3 moves in the circumferential direction, the movable-floor rail 7 is provided with guide portions 18 placed at both sides facing to each outer circumference portion (roller surface) 17 of the movable-floor rollers 6. Thus, the movable-floor rail 7 has a function of preventing detachment of the movable-floor rollers 6, by way of the guide portions 18 provided at the both sides. The outer circumference portions 17 of the movable-floor rollers 6 move while rotating between the guide portions 18. When the irradiation nozzle 1 is at a position where it does not interfere with the movable floor 3, namely, at a non-interfering position shown in FIG. 6, the movable floor is positioned at a height that is the same or nearly the same as an access floor 13 on which a treatment table 25 is placed. When the movable floor 3 is at this non-interfering position, a doctor, a radiological technologist or the like can freely move on the access floor 13 and the movable floor 3.

Using FIG. 2 and FIG. 3, a particle beam therapy system 51 and the particle beam irradiation apparatus 58 will be described. The particle beam therapy system 51 includes a beam generation apparatus 52, a beam transport system 59, and particle beam irradiation apparatuses 58a, 58b. The beam generation apparatus 52 has an ion source (not shown), a pre-accelerator 53, and a charged particle accelerator 54. The particle beam irradiation apparatus 58b is placed in the rotary gantry 19 (see, FIG. 1) so as to constitute the particle beam rotational irradiation apparatus 20. The particle beam irradiation apparatus 58a is placed in a treatment room having no rotary gantry 19. The role of the beam transport system 59 is to communicate between the charged particle accelerator 54 and the particle beam irradiation apparatuses 58a, 58b. The beam transport system 59 is partly placed in the rotary gantry (not shown) and has, at that part, the plurality of bending magnets 22a, 22b, 22c, 22d (see, FIG. 1).

The charged particle beam 31 that is a particle beam, such as a proton beam, etc., generated by the ion source, is accelerated by the pre-accelerator 53 and injected into the charged particle accelerator 54 through an injection device 46. The charged particle accelerator 54 is a synchrotron, for example. The charged particle beam 31 is accelerated up to a given energy. The charged particle beam 31 emitted from an emission device 47 of the charged particle accelerator 54, is transported through the beam transport system 59 to the particle beam irradiation apparatuses 58a, 58b. The particle beam irradiation apparatuses 58a, 58b each radiate the charged particle beam 31 to the diseased site of the patient 45. For the particle beam irradiation apparatuses, numeral 58 is used collectively, and numerals 58a, 58b are used when they are to be described distinctively.

The charged particle beam 31 generated by the beam generation apparatus 52 and accelerated up to the given energy, is brought through the beam transport system 59 to the particle beam irradiation apparatus 58. In FIG. 3, the particle beam irradiation apparatus 58 includes: an X-direction scanning electromagnet 32 and a Y-direction scanning electromagnet 33 which scan the charged particle beam 31, respectively in an X-direction and a Y-direction that are directions perpendicular to the charged particle beam 31; a position monitor 34; a dose monitor 35; a dose-data converter 36; a beam-data processing device 41; a scanning-electromagnet power source 37; and an irradiation management apparatus 38 for controlling the particle beam irradiation apparatus 58. The irradiation management apparatus 38 includes the irradiation control computer 39 and an irradiation control device 40. The dose-data converter 36 includes a trigger generation unit 42, a spot counter 43 and an inter-spot counter 44. Note that in FIG. 3, the travelling direction of the charged particle beam 31 is a direction of −Z.

The X-direction scanning electromagnet 32 is a scanning electromagnet for scanning the charged particle beam 31 in the X-direction, and the Y-direction scanning electromagnet 33 is a scanning electromagnet for scanning the charged particle beam 31 in the Y-direction. With respect to the charged particle beam 31 scanned by the X-direction scanning electromagnet 32 and the Y-direction scanning electromagnet 33, the position monitor 34 detects beam information for calculating a passing position (gravity center position) and a size of the beam that passes therethrough. The beam-data processing device 41 calculates the passing position (gravity center position) and the size of the charged particle beam 31 on the basis of the beam information that comprises a plurality of analog signals detected by the position monitor 34. Further, the beam-data processing device 41 generates an abnormality detection signal indicative of a position abnormality and/or a size abnormality of the charged particle beam 31, and outputs the abnormality detection signal to the irradiation management apparatus 38.

The dose monitor 35 detects the dose of the charged particle beam 31. The irradiation management apparatus 38 controls the irradiation position of the charged particle beam 31 in the diseased site of the patient 45 on the basis of treatment plan data prepared by an unshown treatment plan apparatus, and moves the charged particle beam 31 to a next irradiation position when the dose having been measured by the dose monitor 35 and converted by the dose-data converter 36 into digital data, reaches a desired dose. The scanning-electromagnet power source 37 changes setup currents for the X-direction scanning electromagnet 32 and the Y-direction scanning electromagnet 33 on the basis of control inputs (commands) outputted from the irradiation management apparatus 38 for the X-direction scanning electromagnet 32 and the Y-direction scanning electromagnet 33.

Here, the scanning irradiation method of the particle beam irradiation apparatus 58 is assumed to be a raster-scanning irradiation method in which the charged particle beam 31 is not stopped when the irradiation position of the charged particle beam 31 is changed, that is a method in which the beam irradiation position moves between spot positions successively like a spot-scanning irradiation method. The spot counter 43 serves to measure an amount of irradiation dose during when the beam irradiation position of the charged particle beam 31 is staying. The inter-spot counter 44 serves to measure an amount of irradiation dose during when the beam irradiation position of the charged particle beam 31 is moving. The trigger generation unit 42 serves to generate a dose completion signal when the dose of the charged particle beam 31 at a beam irradiation position reaches the desired irradiation dose.

Next, an operation of the movable floor 3 will be described. Until the irradiation nozzle 1 moves in association with the rotation of the rotary gantry 19 so that the first engaging portion 10 of the irradiation-nozzle support member 12 contacts with the second engaging portion 11 of the movable floor, the movable floor 3 is positioned at the same height as the access floor 13 (non-interfering position) and is locked by the action of the brakes 8 for the movable-floor rollers relative to the rotary gantry 19. On the movable floor 3, there is provided, for example, a contact sensor 26 that detects an occurrence of contact between the first engaging portion 10 and the second engaging portion 11. As the contact sensor 26, a pressure sensor, a distance sensor that detects a distance using infrared rays, or the like, may be used.

When the irradiation nozzle 1 comes close to the movable floor 3 and the coupling portions 9 (jigs for docking) makes a contact with each other, the contact sensor 26 detects its contact state, so that the brakes 8 are placed in a released state to thereby make the movable-floor rollers 6 rotatable. When the irradiation nozzle 1 further moves, the movable floor 3 and the irradiation-nozzle support member 12 are coupled together, thereby causing the movable floor 3 to move in a circumferential direction of the rotary gantry 19 by way of a driving force of a drive motor (not shown) of the rotary gantry 19. When the movable floor 3 and the irradiation-nozzle support member 12 are coupled together, since the movable floor 3 moves together with the irradiation nozzle 1 in the circumferential direction of the rotary gantry 19, the movable floor 3 can be retracted from the irradiation nozzle 1 while keeping constant the distance thereto. The movable floor 3 is retracted in the circumferential direction along the movable-floor rail 7, and at this time, it is always unified with the irradiation nozzle 1. At the time the movable floor 3 is retracted, although the movable floor 3 is inclined relative to the access floor 13, the movable floor 3 is held without dropping out by the guide portions 18 of the movable-floor rail 7.

Next, the operation when the movable floor 3 returns to the non-interfering position from its retracted state, will be described. When the irradiation nozzle 1 is rotated backward from the retracted state where the movable floor 3 and the irradiation nozzle 1 are unified, because of the weight of the movable floor 3 itself, the movable floor 3 returns spontaneously up to the position at the height that is the same or nearly the same as the access floor 13. When it returned up to the height that is the same or nearly the same as the access floor 13 and the contact sensor 26 detected a non-contact state between the first engaging portion 10 and the second engaging portion 11, the brakes 8 lock the movable floor 3 relative to the rotary gantry 19 such that the movable-floor rollers 6 do not rotate.

Description will be made about a floor that allows a doctor or a radiological technologist to set foot thereon when the movable floor 3 is in the retracted state. As shown in FIG. 1, the irradiation-nozzle support member 12 has a plate-like planar portion on which the first engaging portion 10 is placed, and the planar portion serves as a floor on which the doctor or the radiological technologist can ride when the irradiation nozzle 1 is placed at the underside (lower portion) of the rotary gantry. When the irradiation nozzle 1 comes just under the rotation axis of the rotary gantry 19, the planar portion of the irradiation-nozzle support member 12 becomes at the height that is the same or nearly the same as the access floor 13, so that, similarly to the state at the non-interfering position shown in FIG. 6, the doctor, the radiological technologist or the like can freely move on the access floor 13 and the planar portion of the irradiation-nozzle support member 12. Even in this case, the movable floor 3 is being unified with the irradiation nozzle 1 and is thus in the retracted state. When the movable floor 3 is in a retracted state but the planar portion of the irradiation-nozzle support member 12 and the access floor 13 are not at the same or nearly the same height, the movable floor 3 and the planar portion of the irradiation-nozzle support member 12 are inclined relative to the access floor 13; however, it is possible to set foot on the movable floor 3 or the irradiation-nozzle support member 12 when it is in a gently angled state.

Note that, the description has been made using the case where the contact sensor 26 is mounted on the movable floor 3; however, it is allowable not to mount the contact sensor 26 on the movable floor 3 and thus to manually operate the brakes 8 of the movable floor 3. Usually, the doctor, the radiological technologist or the like, stays at a position apart from the movable floor 3 before the rotary gantry 19 is rotated. When the rotary gantry 19 is to be rotated, the doctor, the radiological technologist or the like, manually releases the brakes 8. The releasing timing of the brakes 8 is before the rotary gantry 19 starts rotating. Meanwhile, the operation timing of locking by the brakes 8 is after the movable floor 3 returned to the non-interfering position and the rotation of rotary gantry 19 was stopped.

In the particle beam rotational irradiation apparatus 20 of Embodiment 1, the movable floor 3 can be coupled with the coupling portion 9 of the irradiation-nozzle support member 12. Thus, because of the irradiation nozzle 1 and the movable floor 3 moving in the circumferential direction in a unified manner at the time of movement of the irradiation nozzle 1, the movable floor 3 can be retracted from the irradiation nozzle 1. In the particle beam rotational irradiation apparatus 20 of Embodiment 1, unlike the conventional one in which the movable floor 3 is retracted in the direction of the rotation axis of the rotary gantry 19, the movable floor 3 is retracted in the circumferential direction of the rotary gantry 19. Thus, the movable floor 3 that is retractable at the time of movement of the irradiation nozzle 1 can be placed in the rotary gantry 19. According to the particle beam rotational irradiation apparatus 20 of Embodiment 1, since the movable floor 3 that is retractable at the time of movement of the irradiation nozzle 1 can be placed in the rotary gantry 19, a doctor or a radiological technologist can work in the rotary gantry 19 while setting foot on the movable floor 3. In the case where the movable floor 3 can not be placed in a corkscrew-type particle beam rotational irradiation apparatus, the doctor or the radiological technologist can not go to the deep side of the rotary gantry 19 at the time of working in the rotary gantry. However, the particle beam rotational irradiation apparatus 20 of Embodiment 1 is provided with the movable floor 3 that is retractable at the time of movement of the irradiation nozzle 1, so that the doctor or the radiological technologist can enter into the deep side of the rotary gantry 19 at the time of working in the rotary gantry 19.

The particle beam rotational irradiation apparatus 20 of Embodiment 1 is provided with the movable floor 3 that is retractable at the time of movement of the irradiation nozzle 1 and the irradiation-nozzle support member 12 having the planar portion. Thus, even if the irradiation nozzle 1 is at any angle among 360 degrees, the doctor or the radiological technologist can enter into the deep side of the rotary gantry 19 at the time of working in the rotary gantry 19, to thereby work inside the rotary gantry 19 while setting foot on the movable floor 3 or the planar portion of the irradiation-nozzle support member 12.

The particle beam rotational irradiation apparatus 20 of Embodiment 1 includes: the irradiation nozzle 1 that radiates the charged particle beam 31 to an irradiation target (patient 45); the frame (gantry frame 2) that supports the irradiation nozzle 1 and rotates centering on an isocenter that is an irradiation reference for the charged particle beam 31; the irradiation-nozzle support member 12 that is provided on the inner-circumference side of the frame (gantry frame 2) and supports the irradiation nozzle 1; the movable floor 3 that has rollers (movable-floor rollers 6) movable in the circumferential direction centering on the rotation axis of the frame (gantry frame 2); and the movable-floor rail 7 that is provided in the circumferential direction on the inner-circumference side of the frame (gantry frame 2) and supports the rollers (movable-floor rollers 6); wherein the irradiation-nozzle support member 12 and the movable floor 3 have their respective coupling portions 9 that are attachable/detachable to/from each other. Thus, when the irradiation nozzle comes close to the movable floor, the movable floor and the irradiation nozzle are unified together through the irradiation-nozzle support member, so that the movable floor 60 can move together with the irradiation nozzle in the circumferential direction. Thus, even if it is of a corkscrew type, the movable floor 3 that is retractable at the time of movement of the irradiation nozzle 1 can be placed in the rotary gantry 19.

The particle beam therapy system 51 of Embodiment 1 includes: the beam generation apparatus 52 that generates the charged particle beam 31 and accelerates the charged particle beam 31 using the accelerator (charged particle accelerator 54); the beam transport system 59 that transports the charged particle beam 31 accelerated by the accelerator (charged particle accelerator 54); the irradiation nozzle 1 that radiates the charged particle beam 31 transported by the beam transport system 59 to an irradiation target (patient 45); and the particle beam rotational irradiation apparatus 20 that mounts the irradiation nozzle 1 therein. Thus, when the irradiation nozzle comes close to the movable floor, the movable floor and the irradiation nozzle are unified together through the irradiation-nozzle support member, so that the movable floor can move together with the irradiation nozzle in the circumferential direction. Thus, even in the case of a corkscrew type, the movable floor 3 that is retractable at the time of movement of the irradiation nozzle 1 can be placed in the rotary gantry 19.

DESCRIPTION OF REFERENCE NUMERALS AND SIGNS

1: irradiation nozzle, 2: gantry frame, 3: movable floor, 6: movable-floor roller, 7: movable-floor rail, 9: coupling portion, 12: irradiation-nozzle support member, 13: access floor, 18: guide portion, 20: particle beam rotational irradiation apparatus, 21: beam transport portion, 22a, 22b, 22c, 22d: bending magnets, 25: treatment table, 31: charged particle beam, 45: patient, 51: particle beam therapy system, 52: beam generation apparatus, 54: charged particle accelerator, 58, 58a, 58b: charged particle irradiation apparatuses, 59: beam transport system.

The invention claimed is:

1. A particle beam rotational irradiation apparatus which radiates a charged particle beam in a rotatable manner around an irradiation target, comprising:
   an irradiation nozzle that radiates the charged particle beam to the irradiation target;
   a frame that supports the irradiation nozzle and rotates centering on an isocenter that is an irradiation reference for the charged particle beam;
   an irradiation-nozzle support member that is provided on an inner-circumference side of the frame and supports the irradiation nozzle;
   a movable floor that has a roller movable in a circumferential direction centering on a rotation axis of the frame;
   a brake arranged to release or lock the roller to allow or prevent the roller from rotating; and
   a movable-floor rail that is provided in the circumferential direction on the inner-circumference side of the frame, and supports the roller;
   wherein the irradiation-nozzle support member includes a first coupling portion and the movable floor includes a second coupling portion and the first coupling portion is configured to be attachable/detachable to/from the second coupling portion during operation of the particle beam rotational irradiation apparatus in the circumferential direction centering on the rotation axis of the frame; and
   a sensor configured to detect an attachment/detachment state of the first coupling portion and the second coupling portion for releasing or locking the brake.

2. The particle beam rotational irradiation apparatus of claim 1, wherein the movable-floor rail has at its both ends, guide portions facing to the roller.

3. The particle beam rotational irradiation apparatus of claim 2, wherein, when the movable floor is at a non-interfering position where it does not interfere with the irradiation nozzle, a face of the movable floor placed toward the rotation axis is positioned at a height that is the same or nearly the same as an upper face of an access floor on which a treatment table for moving the irradiation target toward the isocenter is placed.

4. The particle beam rotational irradiation apparatus of claim 2, wherein the irradiation-nozzle support member has a planar portion extending in the inner-circumference side of the frame.

5. The particle beam rotational irradiation apparatus of claim 2, further comprising a beam transport portion that rotates with the frame and leads the charged particle beam into the irradiation nozzle, wherein the beam transport portion has a plurality of bending magnets that are arranged so that a beam path of the charged particle beam is once deviated from a beam transport plane that includes the rotation axis of the frame and an irradiation axis of the irradiation nozzle and then returns to the beam transport plane again.

6. A particle beam therapy system comprising: a beam generation apparatus that generates a charged particle beam and accelerates the charged particle beam using an accelerator; a beam transport system that transports the charged particle beam accelerated by the accelerator; an irradiation nozzle that radiates the charged particle beam transported by the beam transport system to an irradiation target; and the particle beam rotational irradiation apparatus of claim 2 that mounts the irradiation nozzle therein.

7. The particle beam rotational irradiation apparatus of claim 1, wherein, when the movable floor is at a non-interfering position where it does not interfere with the irradiation nozzle, a face of the movable floor placed toward the rotation axis is positioned at a height that is the same or nearly the same as an upper face of an access floor on which a treatment table for moving the irradiation target toward the isocenter is placed.

8. The particle beam rotational irradiation apparatus of claim 7, wherein the irradiation-nozzle support member has a planar portion extending in the inner-circumference side of the frame.

9. The particle beam rotational irradiation apparatus of claim 7, further comprising a beam transport portion that rotates with the frame and leads the charged particle beam into the irradiation nozzle, wherein the beam transport portion has a plurality of bending magnets that are arranged so that a beam path of the charged particle beam is once deviated from a beam transport plane that includes the rotation axis of the frame and an irradiation axis of the irradiation nozzle and then returns to the beam transport plane again.

10. A particle beam therapy system comprising: a beam generation apparatus that generates a charged particle beam and accelerates the charged particle beam using an accelerator; a beam transport system that transports the charged particle beam accelerated by the accelerator; an irradiation nozzle that radiates the charged particle beam transported by the beam transport system to an irradiation target; and the particle beam rotational irradiation apparatus of claim 7 that mounts the irradiation nozzle therein.

11. The particle beam rotational irradiation apparatus of claim 1, wherein the irradiation-nozzle support member has a planar portion extending in the inner-circumference side of the frame.

12. The particle beam rotational irradiation apparatus of claim 11, further comprising a beam transport portion that rotates with the frame and leads the charged particle beam into the irradiation nozzle, wherein the beam transport portion has a plurality of bending magnets that are arranged so that a beam path of the charged particle beam is once deviated from a beam transport plane that includes the rotation axis of the frame and an irradiation axis of the irradiation nozzle and then returns to the beam transport plane again.

13. A particle beam therapy system comprising: a beam generation apparatus that generates a charged particle beam and accelerates the charged particle beam using an accelerator; a beam transport system that transports the charged particle beam accelerated by the accelerator; an irradiation nozzle that radiates the charged particle beam transported by the beam transport system to an irradiation target; and the particle beam rotational irradiation apparatus of claim 11 that mounts the irradiation nozzle therein.

14. The particle beam rotational irradiation apparatus of claim 1, further comprising a beam transport portion that rotates with the frame and leads the charged particle beam into the irradiation nozzle, wherein the beam transport portion has a plurality of bending magnets that are arranged so that a beam path of the charged particle beam is once deviated from a beam transport plane that includes the rotation axis of the frame and an irradiation axis of the irradiation nozzle and then returns to the beam transport plane again.

15. A particle beam therapy system comprising: a beam generation apparatus that generates a charged particle beam and accelerates the charged particle beam using an accelerator; a beam transport system that transports the charged particle beam accelerated by the accelerator; an irradiation nozzle that radiates the charged particle beam transported by the beam transport system to an irradiation target; and the particle beam rotational irradiation apparatus of claim 14 that mounts the irradiation nozzle therein.

16. A particle beam therapy system comprising: a beam generation apparatus that generates a charged particle beam and accelerates the charged particle beam using an accelerator; a beam transport system that transports the charged particle beam accelerated by the accelerator; an irradiation nozzle that radiates the charged particle beam transported by the beam transport system to an irradiation target; and the particle beam rotational irradiation apparatus of claim 1 that mounts the irradiation nozzle therein.

17. The particle beam rotational irradiation apparatus according to claim 1, wherein the movable-floor rail is provided on less than 360° of the inner circumference side of the frame.

* * * * *